(12) United States Patent
Robinson et al.

(10) Patent No.: US 9,291,543 B1
(45) Date of Patent: Mar. 22, 2016

(54) PC BOARD MOUNT CORROSION SENSITIVE SENSOR

(71) Applicant: Sandia Corporation, Albuquerque, NM (US)

(72) Inventors: Alex L. Robinson, Albuquerque, NM (US); Adrian L. Casias, Albuquerque, NM (US); Kent B. Pfeifer, Los Lunas, NM (US); George R. Laguna, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/312,472

(22) Filed: Jun. 23, 2014

(51) Int. Cl.
*G01N 17/00* (2006.01)
*G01N 31/22* (2006.01)
*G01N 31/00* (2006.01)
*G01N 33/28* (2006.01)
*A61K 38/00* (2006.01)

(52) U.S. Cl.
CPC ............. *G01N 17/006* (2013.01); *G01N 31/22* (2013.01)

(58) Field of Classification Search
CPC ....... G01N 17/00; G01N 31/22; G01N 31/00; G01N 33/2888; G01N 33/28; G01N 33/26; G01N 33/00; A61K 38/00; C12Q 1/6827; C12Q 1/6802; C12Q 1/68; C12Q 1/00
USPC ........................................................ 436/6, 2
See application file for complete search history.

(56) References Cited

U.S. PATENT DOCUMENTS

| | | | |
|---|---|---|---|
| 4,278,508 A | 7/1981 | White et al. | |
| 4,874,500 A | 10/1989 | Madou et al. | |
| 5,148,126 A | 9/1992 | Spencer | |
| 5,286,357 A | 2/1994 | Smart et al. | |
| 5,310,471 A | 5/1994 | Markle et al. | |
| 5,469,070 A | 11/1995 | Koluvek | |
| 5,498,914 A | 3/1996 | De Boer | |
| 5,854,557 A | 12/1998 | Tiefnig | |
| 5,959,457 A | 9/1999 | Berberich | |
| 5,972,198 A | 10/1999 | Takeuchi et al. | |
| 6,132,593 A | 10/2000 | Tan | |
| 6,706,091 B1 | 3/2004 | Robinson et al. | |
| 6,768,318 B2 | 7/2004 | Burt et al. | |
| 6,849,168 B2 | 2/2005 | Crumly et al. | |
| 6,897,669 B2 | 5/2005 | Ishio et al. | |
| 7,082,824 B2 | 8/2006 | Lull | |
| 7,708,943 B1 | 5/2010 | Robinson et al. | |
| 7,913,534 B1 | 3/2011 | Robinson et al. | |
| 2005/0269213 A1 | 12/2005 | Steimle et al. | |
| 2007/0163892 A1 | 7/2007 | Haridas | |
| 2010/0001803 A1 | 1/2010 | Ramirez Munoz et al. | |
| 2013/0043892 A1 | 2/2013 | Tu et al. | |

OTHER PUBLICATIONS

U.S. Appl. No. 11/934,996, filed Nov. 5, 2007, Mowry et al.
U.S. Appl. No. 13/253,274, filed Oct. 5, 2011, Allendorf et al.
U.S. Appl. No. 13/633,772, filed Oct. 2, 2012, Allendorf et al.
U.S. Appl. No. 13/711,457, filed Dec. 11, 2012, Robinson et al.
U.S. Appl. No. 14/056,863, filed Oct. 17, 2013, Okandan et al.
U.S. Appl. No. 14/102,422, filed Dec. 10, 2013, Derzon et al.
Sandia National Laboratories, "PC board mountable corrosion sensors," Sandia No. SAND-2013-8592P, Oct. 2013 (2 pages).

*Primary Examiner* — Christine T Mui
(74) *Attorney, Agent, or Firm* — Aman Talwar

(57) ABSTRACT

The present invention relates to surface mount structures including a capacitive element or a resistive element, where the element has a property that is responsive to an environmental condition. In particular examples, the structure can be optionally coupled to a printed circuit board. Other apparatuses, surface mountable structures, and methods of use are described herein.

22 Claims, 14 Drawing Sheets

PC BOARD MOUNT CORROSION SENSITIVE SENSOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD

The present invention relates to surface mount corrosion sensitive capacitors, resistors, and uses thereof.

BACKGROUND

Corrosion is a pervasive and expensive problem in applications ranging from construction to microelectronics. Corrosion has been widely studied in theories, and empirical studies exist for common materials, material combinations, and myriad environmental conditions. In order for microelectronic devices to perform and function properly, a high reliability packaging is important. Failure of microelectronic devices and packages not only causes a malfunction of the devices themselves but can lead to catastrophic events for entire systems, which may cause loss of life, property, and safety.

Corrosion of microelectronic packages and devices depends on the package type, electronic materials, fabrication and assembly processes, as well as environmental conditions, such as moisture condensation, ionic or organic contaminants, temperature, residual and thermal stress, and electrical bias. With the continued reduction of feature sizes of microelectronic device, such devices are more susceptible to corrosion-induced failures. Improved performance and reliability requirements demand improved corrosion resistance.

SUMMARY

The present invention relates to surface mountable sensors for detecting corrosion. In particular, the sensor includes an element responsive to an environmental condition (e.g., atmospheric corrosion, oxidation, aqueous and non-aqueous corrosion, sulfide exposure, moisture condensation, ionic or organic contaminants, temperature, residual and thermal stress, and electrical bias, etc.). In particular, the element includes a corrodible metal configured to provide a capacitive sensor (e.g., employing interdigitated electrodes) or a resistive sensor (e.g., employing a serpentine line). Furthermore, such sensors are configured to be surface mounted on a printed circuit board (PCB). Other sensor structures, apparatuses, and methods are described.

Accordingly, the invention features an apparatus including one or more surface mount structures. In some embodiments, at least one surface mount structure includes a capacitive and/or a resistive element having a property that is responsive to an environmental condition. In other embodiments, the capacitive and/or resistive element may chemically react with species in its environment and corrode. Thus, the apparatus may be used as a corrosion monitor or sensor.

In another aspect, the invention features an apparatus including one or more surface mount structures. In some embodiments, at least one surface mount structure is coupled to a printed circuit board at a first contact point associated with a power circuit and at a second point associated with a ground. In other embodiments, at least one surface mount structure includes a capacitive and/or a resistive element having a property that is responsive to an environmental condition.

In some embodiments, at least one surface mount structure includes a first surface mount structure including a first capacitive and/or resistive element. In further embodiments, the apparatus includes a second surface mount structure including a second capacitive and/or resistive element coupled to the printed circuit board, where each of the first and second elements includes a corrodible metal defined by a layer thickness. In other embodiments, a layer thickness of the corrodible metal of the first surface mount structure is different than a layer thickness of the corrodible metal of the second surface mount structure.

In yet another aspect, the invention includes a method of measuring corrosion. In some embodiments, the method includes providing (e.g., placing) at least one surface mount sensor proximate to an electrical component (e.g., a printed circuit board, a capacitor, a resistor, an inductor, a memristor, a semiconductor, a diode, a transistor, an integrated circuit, a transducer, a sensor, etc.). In other embodiments, the at least one surface mount sensor includes a capacitive and/or a resistive element having a property that is responsive to an environmental condition.

In further embodiments, the method includes measuring a capacitance value and/or a resistance value of the sensor; and relating the measured capacitance and/or resistance to a corrosion experienced by the electrical component.

In some embodiments, measuring a capacitance value includes determining a time to charge an RC circuit including a resistor and the capacitive element.

In other embodiments, the method includes providing a plurality of surface mount sensors proximate to the electrical component, where each of the plurality of surface mount sensor includes a capacitive and/or a resistive element of a corrosive metal. In yet other embodiments, the thickness of the corrosive metal is progressively thicker for the capacitive and/or resistive element of the plurality of surface mount sensors.

In any embodiment herein, the apparatus or method includes a plurality of surface mount structures. Two or more of the surface mount structures can be the same or different. In some embodiments, two or more structures can be the same to ensure redundant monitoring. In other embodiments, two or more structures can be the different to ensure monitoring of different conditions. In particular embodiments, each surface mount structure has a capacitive and/or resistive element of differing thickness. In some embodiments, the apparatus or method includes a reference surface mount structure having a non-corrodible element (e.g., including gold).

In any embodiment herein, the surface mount structure or apparatus includes one or more dimensions (e.g., L, W, T, t, or any described herein) suitable for mounting on a printed circuit board.

In any embodiment herein, the capacitive and/or resistive element may chemically react with species in its environment and corrode. Thus, any apparatus herein may be used as a corrosion monitor or sensor.

In any embodiment herein, the capacitive element includes a corrodible metal, and the structure or apparatus further includes a resistive element. In further embodiments, a time constant associated with the structure changes once the corrodible metal corrodes to reflect a resistance of the resistive element.

In any embodiment herein, the capacitive and/or the resistive element includes a corrodible metal (e.g., copper)

coupled to an adhesion layer on a substrate. In further embodiments, the adhesion layer includes a conductive metal (e.g., titanium).

In any embodiment herein, the capacitive element includes a corrodible metal configured as a pair of interdigitated electrodes. In other embodiments, the capacitive element includes opposing electrodes separated by an air gap.

In any embodiment herein, the resistive element includes a corrodible metal having a serpentine configuration.

As used herein, the term "about" means +/−10% of any recited value. As used herein, this term modifies any recited value, range of values, or endpoints of one or more ranges.

As used herein, the term "semiconductor" should be understood broadly as including semimetals, semi-insulators, and the like.

As used herein, the term "metal" should likewise be understood broadly as including metal and metallic alloys and the like.

As used herein, the terms "top," "bottom," "upper," "lower," "above," and "below" are used to provide a relative relationship between structures. The use of these terms does not indicate or require that a particular structure must be located at a particular location in the apparatus.

DETAILED DESCRIPTION

The present invention relates to surface mountable sensors. In particular, these sensors include a capacitive or resistive element having a property that is responsive to an environmental condition. An exemplary material having such a property is copper. Upon exposure to an environmental condition such as oxygen, copper oxidizes, and its capacitance and resistance values change. This change can be detected using a simplified circuit. Thus, the sensors of the invention are capable of detecting one or more environmental conditions.

In addition, the surface mountable sensors of the invention can be configured to have other benefits. For instance, the sensors can be formed easily and at low cost employing established microfabrication techniques to form numerous sensors on a single wafer. In another instance, the dimensions and design parameters can employ industry standardized sizes, thereby facilitating PCB design and simplifying integration on the PCB. In yet another instance, the sensors can include a solderable material or include pre-tinned surfaces to ease soldering onto a PCB. Finally, the sensors can be simple to operate and/or have low power consumption.

In general, the present invention encompasses two differing types of sensors: capacitive sensors and resistive sensors. Details of sensors, apparatuses, and methods follow.

Capacitive Sensors

A capacitive sensor includes at least one capacitive element. In particular, this element has a property that is responsive to an environmental condition. Exemplary sensors include those having interdigitated electrodes (e.g. as shown in FIGS. 1A-1D, 2A-2D, and 3) and those having an air gap (e.g., as shown in FIGS. 11A-11C and 15A-15B).

Figure 1A:
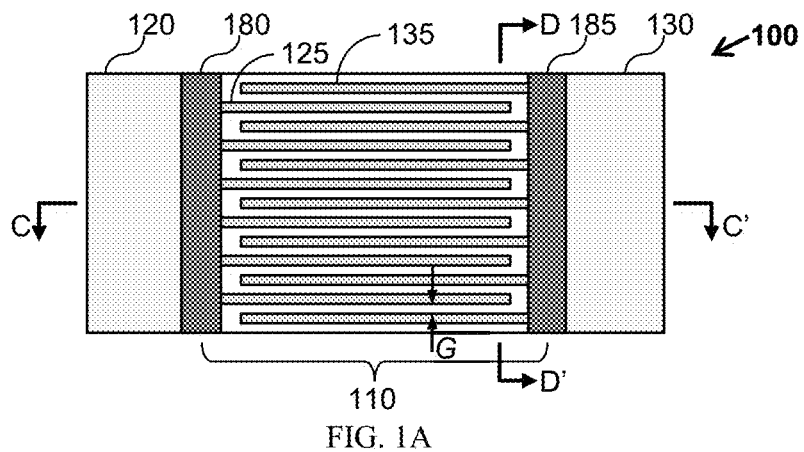
FIG. 1A-1D shows an exemplary surface mount structure 100 including a capacitive element 110. Provided are (A) a top view, (B) an end side view, (C) a side view through line C-C' in FIG. 1A, and (D) a side view through line D-D' in FIG. 1A.
Figure 1B:
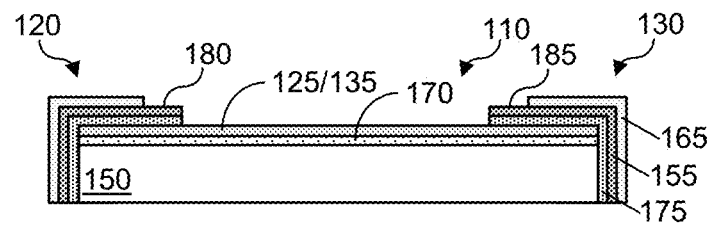

In one embodiment, the sensor is a surface mount structure including a capacitive element. An exemplary capacitive sensor is shown in FIG. 1A-1D. As shown in FIG. 1A-1B, the structure 100 includes a capacitive element 110. The capacitive element 110 is defined by one or more bond pads or bus bars 120, 130. In some embodiments, each bond pad or bus bar has a number of electrodes or electrode pairs 125, 135 extending therefrom.

As shown in FIG. 1B, the structure 100 includes a substrate 150, such as a ceramic, alumina, or silicon substrate, onto which the capacitive element (e.g., a capacitor including interdigitated electrodes) is formed. An optional adhesion layer 170 can be disposed on the top surface of the substrate.

Figure 1C:
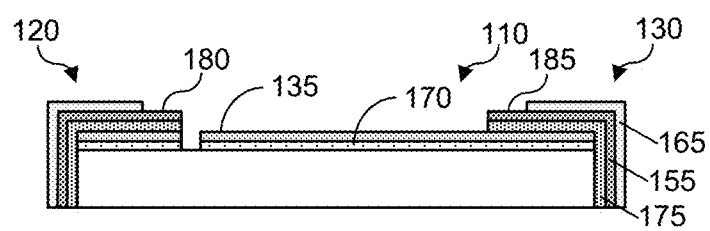
Figure 1D:

In one non-limiting example, the capacitive element includes an interdigitated arrangement with first electrodes 125 that are electrically connected to a first bus bar 120 and second electrodes 135 extending from a second bus bar 130. Each electrode extends across at least a portion of the top surface of the substrate (FIG. 1C). The electrodes 125, 135 are interdigitated electrodes (IDEs), in the sense that they appear to interlock on the top surface of the substrate 150 (FIG. 1D). The electrodes can be formed of any useful material (e.g., a conductive and/or a corrodible material, such as any described herein).

In another non-limiting example, the bus bars or bond pads may include a solder compatible material. For instance, the bus bars 120, 130 may be coated with a solder compatible material 155 (e.g., nickel or any described herein) for suitable soldering of the structure 100 to a surface (e.g., of a printed circuit board). Optionally, the bus bars 120, 130 can further include an oxidation inhibitor layer 165 (e.g., gold or any described herein). Thus, each bus bar may include gold plated nickel as a solder pad material. In yet another option, the bus bars 120, 130 may include an adhesion material 175 disposed between the solder compatible material 155 and a portion of the electrode layer 125/135. In particular embodiments, the adhesion material 175 is disposed on a portion of the top surface and/or edges of the structure.

The structures can optionally include one or more solder barriers or solder dams. Such barriers and dams minimize contact of solder with a sensitive structure (e.g., the capacitive element, such as electrodes) during a soldering of the structure to a printed circuit board or package.

Figure 2A:
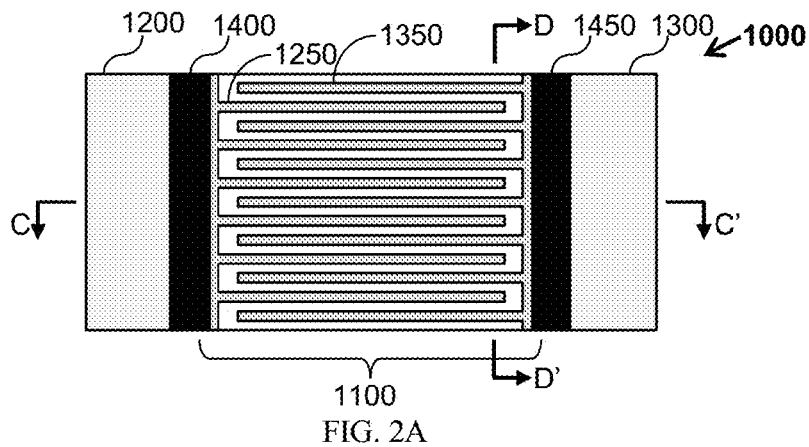
FIG. 2A-2D shows another exemplary surface mount structure 1000 including a capacitive element 1100 and solder barriers 1400, 1450. Provided are (A) a top view, (B) an end side view, (C) a side view through line C-C' in FIG. 2A, and (D) a side view through line D-D' in FIG. 2A.

As shown in FIG. 1A, the structure 100 includes one or more solder barriers 180, 185, which minimizes contact of solder with a sensitive structure (e.g., the capacitive element, such as electrodes) during a soldering of structure to a printed circuit board or package (FIG. 1A). Alternatively, the sensor can include one or more solder dams 1400, 1450 (FIG. 2A).

Figure 2B:
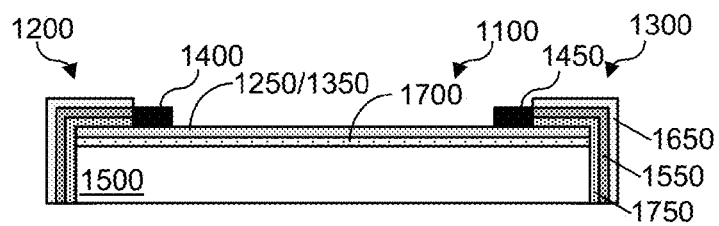
Figure 2C:
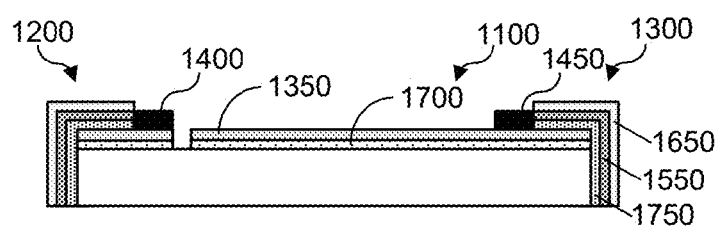
Figure 2D:
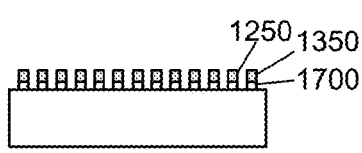
Figure 3:
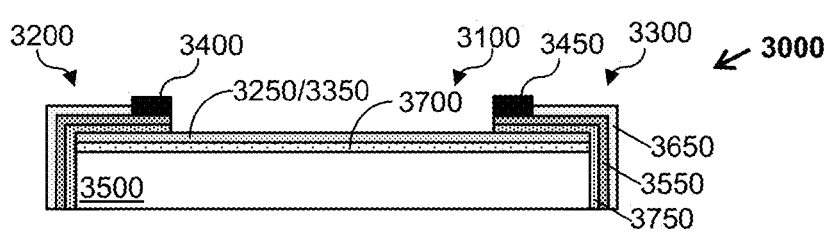
FIG. 3 shows yet another exemplary surface mount structure 3000 showing an alternative, non-limiting placement of solder barriers 3400, 3450 on a top surface of layer 3550.

Both solder dams and solder barriers can include any useful solder-repellant material (e.g., nickel or a polymer, such as polyimide, or any described herein) and can be configured as appropriate (e.g., positioned on one or more bus bars and/or laterally extending across one or more bus bars). In one embodiment, the solder dams 1400, 1450 are disposed on a portion of a top surface of the electrode layer 1250/1350 (FIG. 2B). If the solder-repellant material has minimal wettability with the solder, then placing solder on the bus bar or bond pad should minimize contaminating the electrode layer with the solder material. Alternatively, the solder dams 3400, 3450 can be disposed on a portion of the solder compatible layer 3550 and/or have a thickness greater than that of the oxidation inhibitor layer 3650 (FIG. 3). In this configuration, the solder dam forms a physical barrier to contamination and, if composed of a solder-repellant material having minimal wettability with the solder, then also will minimize wetting of the solder.

To complete the discussion regarding FIG. 2A-2D, an exemplary structure 1000 can include a capacitive element 1100; one or more bus bars 1200, 1300; a number of electrodes or electrode pairs 1250, 1350 extending therefrom; one or more solder dams 1400, 1450; and an optional adhesion layer 1700 disposed on the substrate 1500 to promote adhesion of the electrode layer 1250/1350 to the substrate. Each bus bar can include an optional adhesion layer 1750 to promote adhesion of the solder compatible layer 1550 to the electrode layer 1250/1350, as well as include an optional oxidation inhibitor layer 1650.

To complete the discussion regarding FIG. 3, an exemplary structure 3000 can include a capacitive element 3100; one or more bus bars 3200, 3300; an electrode layer 3250/3350; one or more solder dams 3400, 3450; an optional adhesion layer 3700 disposed on the substrate 3500; an optional adhesion layer 3750 for the bus bar; a solder compatible layer 3550; and an oxidation inhibitor layer 3650.

Optional adhesion layers can be present in the structure. For example, as shown in FIG. 3, an adhesion layer 3700 can be located between the substrate 3500 and the electrode layer 3700. As also shown in this figure, another adhesion layer 3750 may be located between the electrode layer 3250/3350 and the solder compatible layer 3550. In another example, as shown in FIG. 1B, adhesion layer 170 underlies each interdigitated electrode 125, 135 and each bus bar 120, 130. In particular, such adhesion layers promote contact between two or more planar or non-planar surfaces. In one embodiment, the adhesion layer assists the adhesion of a conductive and corrodible material for electrodes and bus bars to the substrate.

The adhesion layer can include one or more useful adhesion materials (e.g., any described herein), including those that are conductive (e.g., to ensure electrical contact between two or more components, such as the bond pad and the electrode, in the structure). The adhesion layer can be continuous, substantially continuous, or discontinuous between the two or more components. Finally, the adhesion layer can be disposed on any useful surface of the structure, such as on the top, side, edge, and/or bottom surfaces exposed when fabricating the sensor.

Figure 4A:
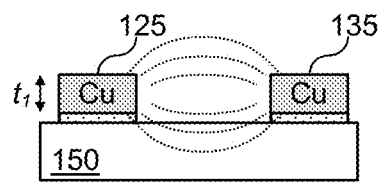
FIG. 4A-4B shows the capacitive field (dashed lines) between two opposing electrode elements 125, 135. Provided are fields (A) before and (B) after corrosion of the electrode materials.
Figure 4B:
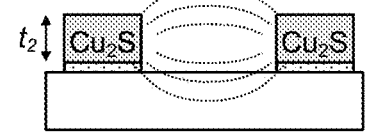

In use, interdigitated electrodes can detect the presence of an environmental condition based on how this condition affects the electrode material's properties. For instance, FIG. 4A shows a magnified view of two interdigitated electrodes 125, 135 on a substrate 150. FIG. 4B shows the same adjacent electrodes following corrosion of the electrodes.

In the embodiment shown in FIG. 4A-4B, the electrode material is copper metal. Copper metal is responsive (e.g., reactive) and, in the presence of sulfide in the environment (e.g., $H_2S$, $HS^-$, and/or $S^{2-}$), will form copper sulfide, e.g., Cu₂S. As seen in FIG. 4A, prior to corrosion of copper, the electrodes have a thickness $t_1$. Before any corrosion, the structure will have a certain capacitance. As the copper corrodes and becomes copper sulfide, the capacitance value will change. FIG. 4B shows copper becoming corroded to copper sulfide. As the electrode material corrodes, it undergoes an expansion, where electrode thickness $t_2 > t_1$. The gap or distance between the electrodes is reduced because of this growth, which modifies the capacitance.

Further, copper sulfide has a different permittivity or dielectric constant than copper, and the difference in dielectric constant will also affect the capacitance value of the sensor. In addition, the electrode's internal resistance increases as the cross-section of conductive metal decreases. These factors both contribute to an increase in the RC time constant, where the time constant is defined as the product of the total effective resistance and the capacitance of the sensor or the sensor in a circuit containing a resistor in series with the sensor.

Figure 11A:
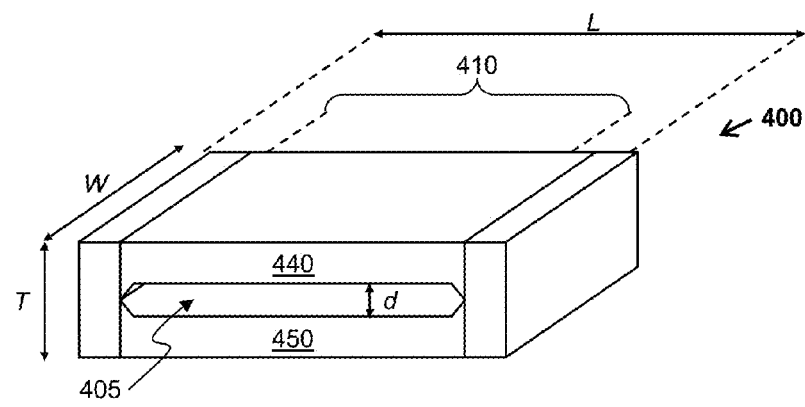
FIG. 11A-11C shows another embodiment of a surface mount structure 400 including a capacitive element 410. Provided are (A) a perspective view, (B) an end side view, and (C) a top side view.
Figure 11B:
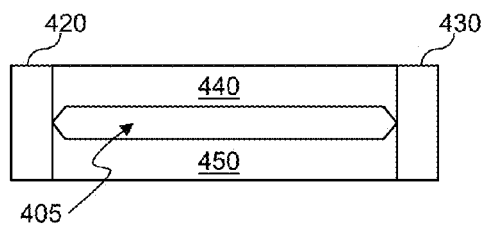
Figure 11C:
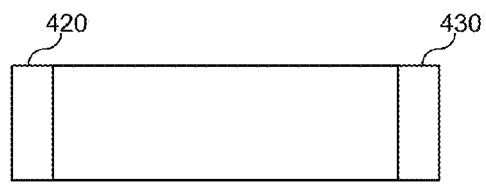

The capacitive element can include any useful structures. As an alternative to IDEs, the capacitive element can include a gap between two plates to form a parallel capacitor electrode pair. FIG. 11A-11C shows an exemplary structure 400 having such a capacitive element 410. The structure 400 is formed of two substrates 440, 450, such as ceramic, alumina or silicon substrates, onto which a conductive and corrodible electrode material, such as copper or aluminum, is formed. The substrates are bonded together to form a parallel capacitor electrode pair. Exemplary electrode configurations are provided in FIG. 13E (electrode layer 630) and FIG. 15A-15B (electrode layers 631, 632).

The corresponding electrodes are separated by distance d 405 that allows for the diffusion of gases and partially determines the capacitance value. The surface mount structure 400 also includes end caps or bus bars 420, 430. In one embodiment, the conductive and corrodible metal of the electrodes is responsive to an environmental condition or a change in environmental condition including corrosion. Accordingly, capacitance will change as the conductive and corrodible metal corrodes according to the theoretical equation:

$$C = \frac{\varepsilon A}{d},$$

where C is capacitance; $\varepsilon$ is the permittivity of non-conductive materials between plates; A is the area between plates; and d is the distance between plates. Initial C can be tailored by the dimensions of the parallel plates (A) and the depth of the gap (d). Initial C can range from nanoFarad ($10^{-9}$ F) to sub-femtoFarad (e.g., $10^{-15}$ F). The substrates and structure can have any useful dimension. For instance, representative dimensions include L of about 4 mm, W of about 2 mm, T of about 0.7 mm, and d of about 100 μm (see FIG. 11A), thereby providing sensing dimensions of, for example, 2 mm×2 mm×100 μm, where A is 2 mm×2 mm.

Figure 8:
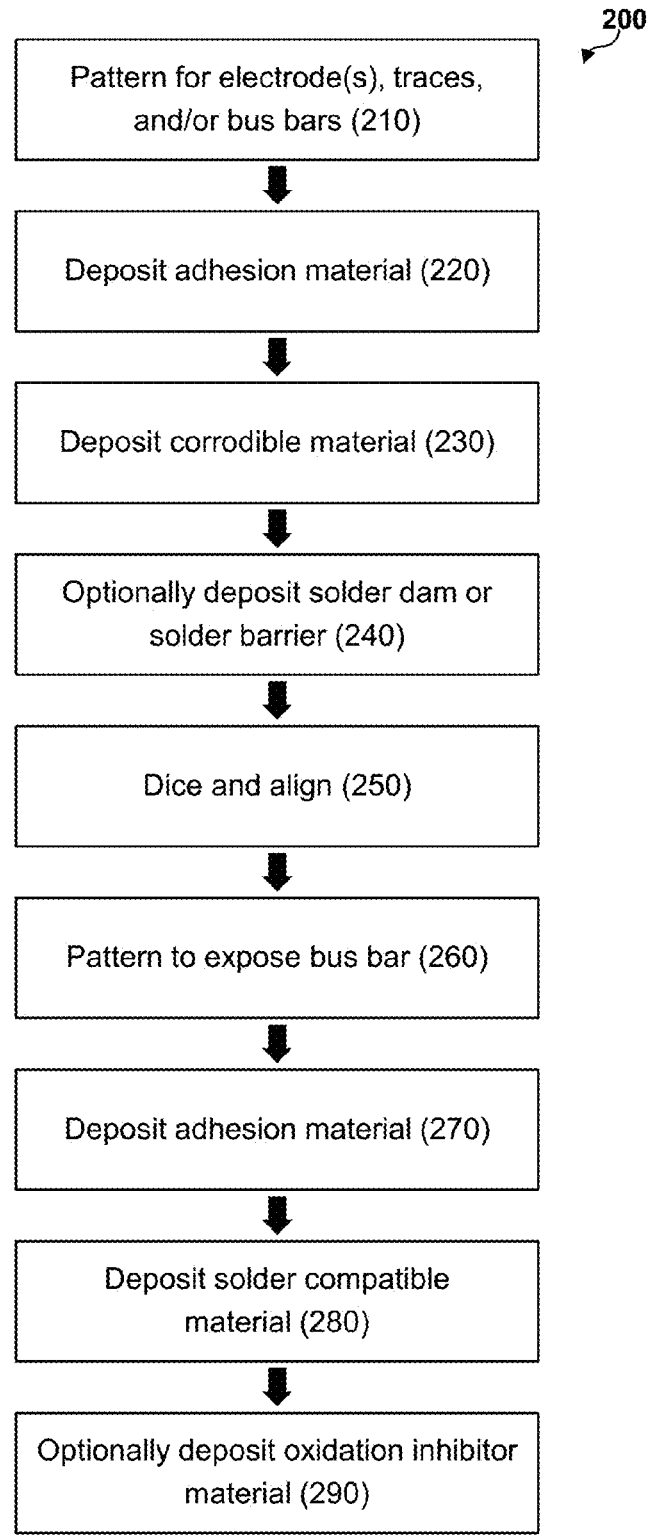
FIG. 8 shows a flow chart for an embodiment of forming a surface mount structure 200.

The capacitive sensors can be fabricated using any useful technique or method. Exemplary, non-limiting methods are provided in FIGS. 8 and 12, described herein.

Resistive Sensors

A resistive sensor includes at least one resistive element. In particular, this element has a property that is responsive to an environmental condition. Exemplary sensors include those having a resistive element (e.g., as shown in FIG. 5A-5B).

Figure 5A:
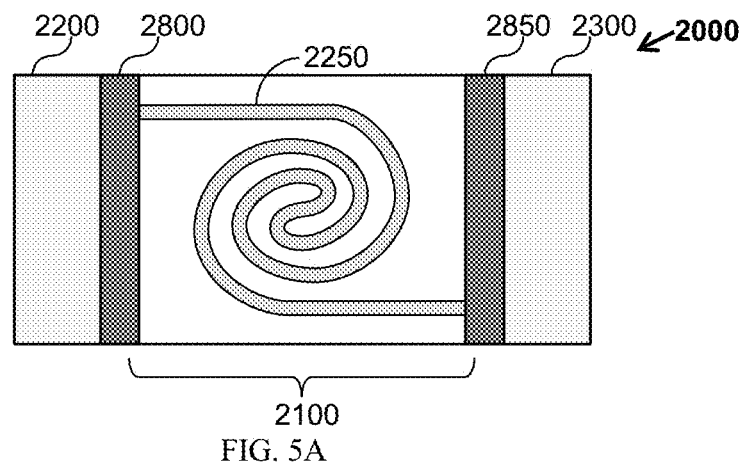
FIG. 5A-5B shows an exemplary surface mount structure 2000 having a resistive element 2250. Provided are (A) a top view and (B) a side view.

In one embodiment, the sensor is a surface mount structure 2000 including a resistive element 2100 (FIG. 5A). The resistive element 2100 is defined by a resistive trace 2250 electrically connected to one or more bond pads or bus bars 2200, 2300. The resistive trace 2250 can have any useful dimension, such as trace thickness, width (e.g., different widths can tune initial resistance for each thickness to similar values), and length, and configuration (e.g., a serpentine or zigzag pattern).

Figure 5B:
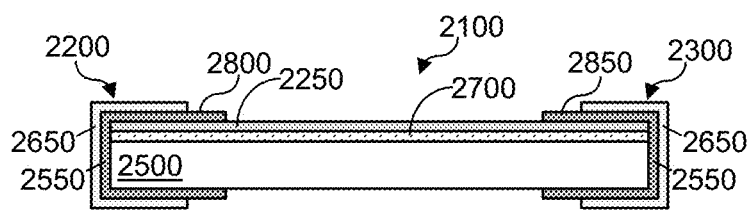

As shown in FIG. 5B, the structure 2000 includes a substrate 2500, such as a ceramic, alumina, or silicon substrate, onto which the resistive element (e.g., a resistor including a metal trace) is formed. An optional adhesion layer 2700 can be disposed on the top surface of the substrate. The structure can also include one or more optional solder barriers 2800, 2850. Similar to the capacitive sensor, the bus bar or bond pad can include any useful layers, including a solder compatible layer 2550 and/or an oxidation inhibitor layer 2650.

The resistive sensors can be fabricated using any useful technique or method. An exemplary, non-limiting method is provided in FIG. 8, described herein.

Surface Mountable Sensors

Figure 6:
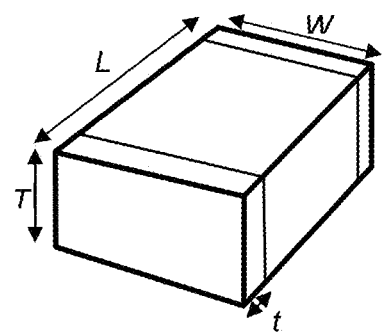
FIG. 6 shows a schematic of various dimensions of the surface mount sensor.

The surface mountable sensors of the invention include any sensor described herein (e.g., capacitive and/or resistive sensors). In particular embodiments, the sensor is configured to have any useful dimension for PCB integration. FIG. 6 provides some of these dimensions, including length L between the terminals (e.g., bond pads or bus bars), the width W, the thickness T, and the terminal length t.

Exemplary dimensions include L of about 10 mm or less (e.g., 5 mm or less, such as about 0.5 mm); W of about 10 mm or less (e.g., 2 mm of less, such as about 0.5 mm); T of about 5 mm or less (e.g., 1 mm or less, such as about 0.6 mm or about 0.1 mm); and t of about 2 mm or less (e.g., about 1 mm). In some embodiments, the dimensions reflect an industry standardized size, e.g., metric size code 4520 of about 4.57 mm×2.03 mm (about 0.18"×0.080" for comparable inch size code 1808); metric size code 2012 of about 2.0 mm×1.25 mm (about 0.079"×0.049" for comparable inch size code 0805); metric size code 3225 for 3.2 mm×2.5 mm (about 0.126"×0.098" for comparable inch size code 1210); and metric size code 5025 of about 5.0 mm×2.5 mm (about 0.197"×0.098" for comparable inch size code 2010), all provided as L×W. In other embodiments, the structure includes at least one of a length L of dimensions up to 10 mm, a width W of 10 mm, and a thickness T of 5 mm; and dimensions larger than at least one of a length L of 10 mm, a width W of 10 mm, and a thickness T of 5 mm.

Other dimensions include those related to the electrode or the trace for the capacitive or resistive element. These dimensions include thickness of the electrode layer or the trace layer $e_t$ (e.g., of from about 200 Å to about 2500 Å) (see, e.g., FIG. 21B), electrode or trace width $e_w$ (e.g., about 10 nm to about 100 μm, such as from 10 nm to 30 μm, 5 μm to 100 μm, or about 10 μm) (see, e.g., FIG. 21A), gap G between electrode (e.g., from about 1 μm to about 100 μm, such as about 10 μm) (see, e.g., FIGS. 1A and 21A), distance d between plates (e.g., from about 50 μm to about 500 μm) (see, e.g., FIG. 11A), electrode or tracer length $e_L$ (e.g., about 1 mm to about 500 mm), overlap of electrode $e_o$ (e.g., from about 0.5 mm to 4 mm, such as about 2 mm) (see, e.g., FIG. 21A), and n number of electrodes or traces (e.g., n of from 10 to about 100, such as from 10 to 20, 10 to 50, 10 to 100, 20 to 50, 20 to 100, and 50 to 100). Exemplary numerical ranges for these parameters are provided herein.

In general, there is no minimum on $e_w$, the width of the electrodes. However, greater overlap $e_o$ tends to provide greater capacitance. In another embodiment, there could be fewer interdigitated electrodes and even no interdigitated electrodes in an embodiment where, for example, the working area (e.g., the sensing area or capacitive element) is defined by the gap between two opposing corrodible metal strips.

The sensors can be provided as an array. For instance, the surface mountable array can include a plurality of sensors, where each sensor is configured to be suitable for mounting on a printed circuit board. The array can include capacitive sensors and/or resistive sensors. Within the array, two or more sensors can be different or same. For example, the array may include two or more of the same sensors to provide redundant measurements. In another example, the array may include two or more different sensors that are optimized to measure different environmental conditions (e.g., different exposures, such as a contaminant exposure and a moisture exposure; and/or different levels of the same exposure, such as different levels of the same contaminant). Thus, the array can include one or more subarrays of sensors. For example, the first subarray can include a plurality of a first sensor, and the second subarray can include a plurality of a second sensor, where each first sensor in the first subarray can be the same or different, and each second sensor in the second subarray can be the same or different. In further embodiments, the array includes one or more reference sensors (e.g., a sensor having a non-corrodible material, such as a gold trace).

Figure 7:
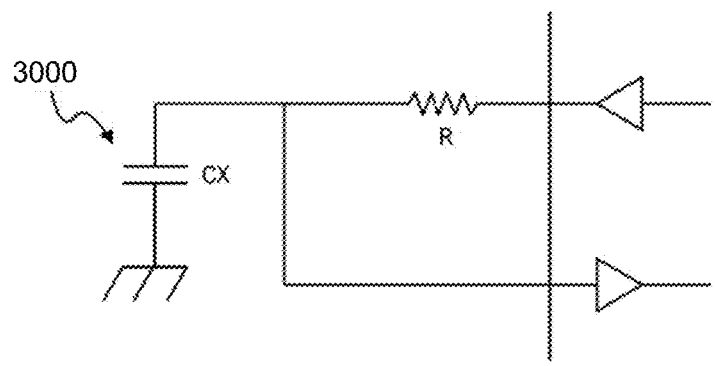
FIG. 7 shows a simple and low-power embodiment of an electrical circuit whereby the sensor 3000 (e.g., a capacitive or resistive sensor) is part of the circuit and changes in the sensor are readily observable as changes in electrical properties of the circuit.

The capacitance or resistance of the sensor can be determined by any useful method. FIG. 7 shows an exemplary circuit having a fixed resistance and a variable capacitance represented by, for example, a structure 3000 that is a capacitive sensor. Such circuit may be charged by a capacitance meter or any circuit programmed to charge the capacitor and measure its capacitance such as a field programmable array (FPGA) or application specific integrated circuit (ASIC). Alternatively, the circuit can include a structure that is a resistive sensor (e.g., any described herein) in combination with a reference resistor (e.g., R in FIG. 7) or one or more other resistors or pairs of resistors (e.g., as in a four-terminal sensing method). In this manner, an ohmmeter can be used to measure the change in resistance. The RC time constant or resistance for any of these circuits can be measured as the charge voltage rises above a threshold (e.g., ½ the charging voltage or $\Delta R/R$ is 50%) or falls from a fully charged state to below a threshold. Changes in the RC time constant or resistance reflect changes to the capacitive and/or resistive structure. Other non-limiting circuits include those in U.S. Pat. Nos. 5,148,126, 5,469,070, 5,498,914, 5,959,457, 6,768,318, and 7,082,824; and U.S. Pub. Nos. 2010-0001803 and 2013-0043892, each of which is incorporated by reference herein in its entirety.

Materials

The sensors of the invention can include one or more material(s) provided in any useful form (e.g., layers, including continuous or substantially continuous layers disposed on a surface or a portion thereof; discs; films; patterns; etc.).

Any useful material can be employed. For instance, the substrate can be formed of an insulator material (e.g., a ceramic, such as alumina) or includes an insulative material (e.g., $SiO_2$ on silicon). Thus, exemplary substrate materials include ceramic (e.g., alumina), glass, quartz, or silicon, including any useful for microfabrication or semiconductor fabrication.

The capacitive or resistive elements can be formed of one or more materials that are responsive to an environmental condition. Exemplary materials include conductive materials (e.g., a metal, such as copper, silver, or aluminum, as well as alloys thereof or graphite), a polymer (e.g., a conductive polymer and/or a stimuli responsive polymer), or a corrodible material (e.g., copper, a copper alloy, or an aluminum alloy, such as an aluminum/copper alloy, an aluminum/silicon alloy, an aluminum/silicon/copper alloy, etc.). In certain embodiments, the material is both conductive and corrodible (e.g., copper or an alloy thereof).

Electrical connection of the capacitive or resistive element is achieved by using bus bars and/or solder pads. Thus, bus bars and solder pads can be formed of any useful solder compatible material or include a layer of such a material. Exemplary solder compatible materials include nickel, as well as alloys thereof. To minimize oxidation, the solder compatible material can include a coating or a layer of an oxidation inhibitor material, e.g., gold. To facilitate soldering, the bus bar and/or solder pads can include a layer of tin.

The solder dams and barriers reduce the likelihood of solder contacting the capacitive or resistive elements. This reduction can be achieved by using materials having reduced wettability for the solder and/or having melting or softening temperatures above the temperature for performing soldering. Exemplary solder-repellant materials include nickel, tantalum nitride, titanium tungsten, as well as alloys thereof or a polymer, such as polyimide, As described herein, one or more adhesion materials and layers thereof can be used to contact one surface to another. Exemplary adhesion materials include chromium, titanium, nickel, as well as alloys thereof.

Methods of Fabricating Sensors

The sensors of the invention can be fabricated using any useful technique. In particular, these sensors are fabricated using microfabrication or semiconductor fabrication techniques. Exemplary methods of fabrication include rapid prototyping, microfabrication (e.g., by casting, injection molding, compression molding, embossing, ablation, thin-film deposition, and/or Computer Numerically Controlled (CNC) micromachining), photolithography, and/or etching techniques (e.g., wet chemical etching, reactive ion etching, inductively coupled plasma deep silicon etching, laser ablation, or air abrasion techniques).

In one non-limiting embodiment, the sensor (e.g., a capacitive and/or resistive sensor) is fabricated using the process 200 shown in FIGS. 8, 9A-9B, and 10A-10C. The process 200 starts from a wafer (e.g., a four-inch diameter ceramic, alumina or silicon wafer) having designated areas for forming multiple structures. A surface of the wafer is patterned for the electrode(s), traces(s), and/or bus bar(s) (block 210). Representatively, the surface of the wafer may be patterned using photolithographic techniques.

Once openings for the electrode(s), traces(s), and/or bus bar(s) are patterned, an adhesion material is deposited (block 220) (e.g., as an adhesion layer). In one embodiment, the adhesion layer is a titanium material (e.g., pure titanium metal) of a thickness on the order of 200 μm. The adhesion layer material may be deposited by chemical vapor deposition (CVD) or sputtering technique.

Next, material for the electrode(s), traces(s), and/or bus bar(s) is deposited (block 230). In one embodiment, the material for the electrodes, traces, and/or bus bars is a conductive and corrodible material, such as copper, aluminum, or alloys thereof. It is appreciated that for use as a corrosion sensor, a thickness of the conductive and corrodible material will determine the sensor life because a thinner layer of corrodible material will corrode to completion faster than a thicker layer. Representative thicknesses include 500 Å to 2000 Å or more. Such deposition may be accomplished by CVD, sputtering, or electrochemical or electroless plating baths.

Following the deposition of conductive and/or corrodible material, solder dams/barriers may optionally be added (block 240). In one embodiment, to add solder dam, a photolithographic mask is patterned to cover the electrode area and portions of the bus bars and leave an area of the bus bars extending laterally across the bus bars available for solder dam material. A solder dam material of, for example, a nickel material may be deposited via CVD or sputtering. A representative thickness is on the order of one to five μm.

Figure 9A:
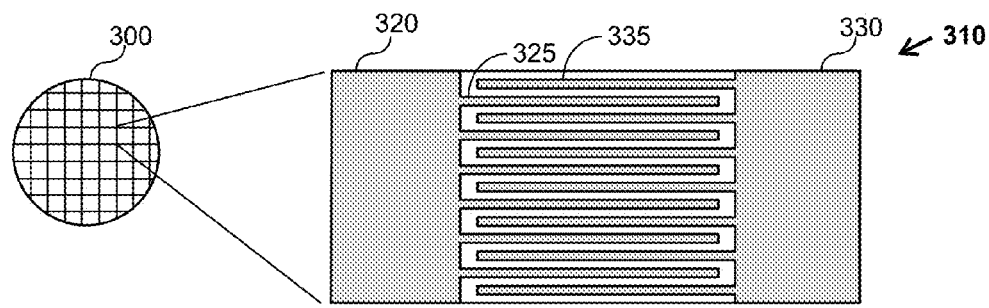
FIG. 9A-9B shows a top view of a wafer 300 having a number of defined areas for structure formation. Also provided is (A) a top view of one structure area 310 having electrodes and bus bars patterned over an adhesion layer formed thereon and (B) a top view of one structure area 315 having optional solder dams 340, 345 formed on each bus bar.
Figure 9B:
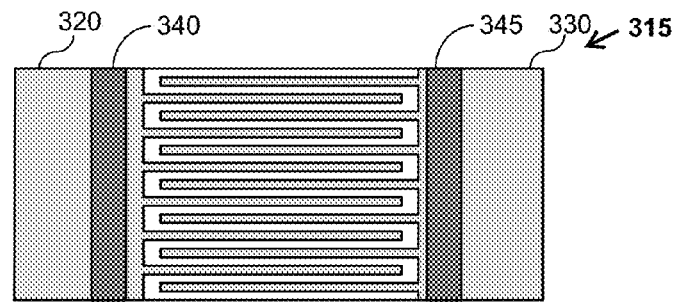

FIG. 9A shows a top view of wafer 300 having a number of defined areas for structure formation. One area exploded representing structure 310 in this view shows a surface of a substrate having electrodes and bus bars of a corrodible material patterned thereon. FIG. 9A shows bus bar 320 having electrodes 325 extending therefrom and bus bar 330 having electrodes 335 extending therefrom to define an interdigitated electrode structure. FIG. 9B shows a structure 315 following the deposition of optional solder dams 340 and 345 on portion of bus bars, 320 and 330, respectively. FIG. 9B also shows structure 315 following the removal of any photolithographic masking material from a surface of the electrodes and the bus bars. To form a resistive sensor, one or more traces and/or bus bars can be deposited on the substrate.

Returning to FIG. 8, in one embodiment, following the optional deposition of optional solder dams, the wafer may be singulated to define individual structures. The individual structures may be aligned (grouped) for further processing (block 250).

Following alignment, a surface of each singulated substrate is patterned with, for example, a photolithographic material to expose a portion of the bus bar and protect the electrodes (block 260). Next, an adhesion material is deposited on the exposed bus bar (block 270) (e.g., as an adhesion layer). A suitable adhesion layer material is, for example, a titanium or chromium material. A representative thickness is on the order of 200 Å.

Next, a solder compatible material is deposited by CVD, sputtering or electrochemical or electroless plating baths (block 280) over the adhesion material or layer.

Then, optionally, an oxidation inhibitor is deposited (block 290). An oxidation inhibitor is a material that inhibits the oxidation or contamination of the solder compatible material. For a representative solder compatible material that is a nickel material, a suitable oxidation inhibitor is a gold material (pure gold or an alloy) deposited to a thickness of approximately up to 100 Å by CVD, sputtering, or electroplating.

Once process 200 has been completed, the obtained structure 310 and any other useful structure(s) may be connected to a printed circuit board, a package or other desired platform for use as a sensor (e.g., a corrosion sensor). In one embodiment, structure 310 is inverted to connect to the platform (e.g., a printed circuit board).

Figure 10A:
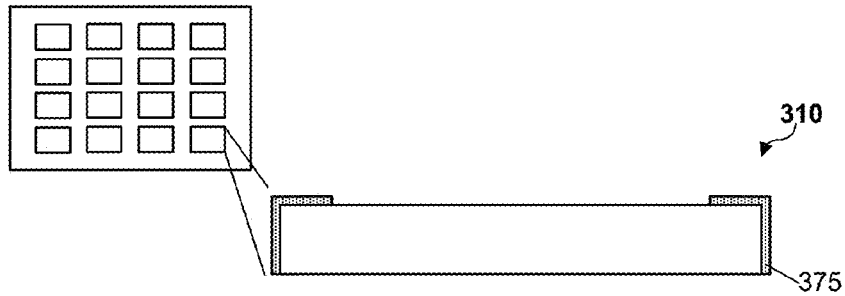
FIG. 10A-10C shows a top view of a number of aligned structures following singulation from a wafer and a side view of a structure 310 after various process steps. Provided are side views of structure 310 having (A) an adhesion layer 375 formed on the bus bars, (B) a solder compatible material 355 on the bus bars, and (C) an oxidation inhibitor material layer 365 on the bus bars.
Figure 10B:
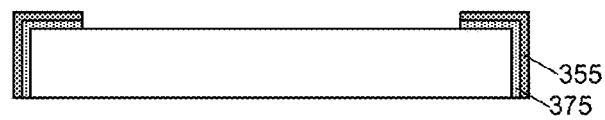
Figure 10C:
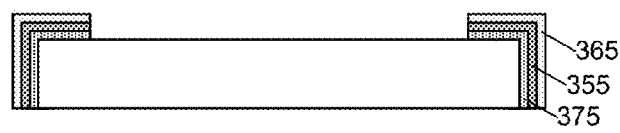

FIG. 10A-10C shows exemplary embodiments of steps 270, 280, and 290. FIG. 10A shows a side view of several aligned singulated substrates and shows a side view of substrate 310 having adhesion layer 375 deposited on a surface by CVD or sputtering. Adhesion layer 375 is deposited not only on a surface including bus bar 320 and bus bar 330, but, in one embodiment, may extend on one or more side walls and even to the underside of the structure as viewed.

FIG. 10B shows structure 310 having a solder compatible material layer 355 deposited over adhesion layer 375. In one embodiment, a solder compatible material is a nickel material (e.g., nickel metal or alloy). Solder compatible material layer 355 is deposited to at least a thickness suitable to accommodate a solder connection between the solder compatible material and another substrate (e.g., a printed circuit board). Representatively, a suitable thickness is on the order of 0.9 microns to 2.5 microns. Solder compatible material layer 355 may extend on one or more side walls and even to the underside of the structure.

FIG. 10C shows substrate 310 following the deposition of an oxidation inhibitor material layer 365 over the solder compatible material 355 shown in FIG. 10B. In FIG. 10C, only the top of structure 310 (as viewed) and one side wall is shown with an adhesion layer 375, a solder compatible material layer 355, and an oxidation inhibitor layer 365. It is appreciated that each layer may extend to the other side walls and the underside of structure 310.

Figure 12:
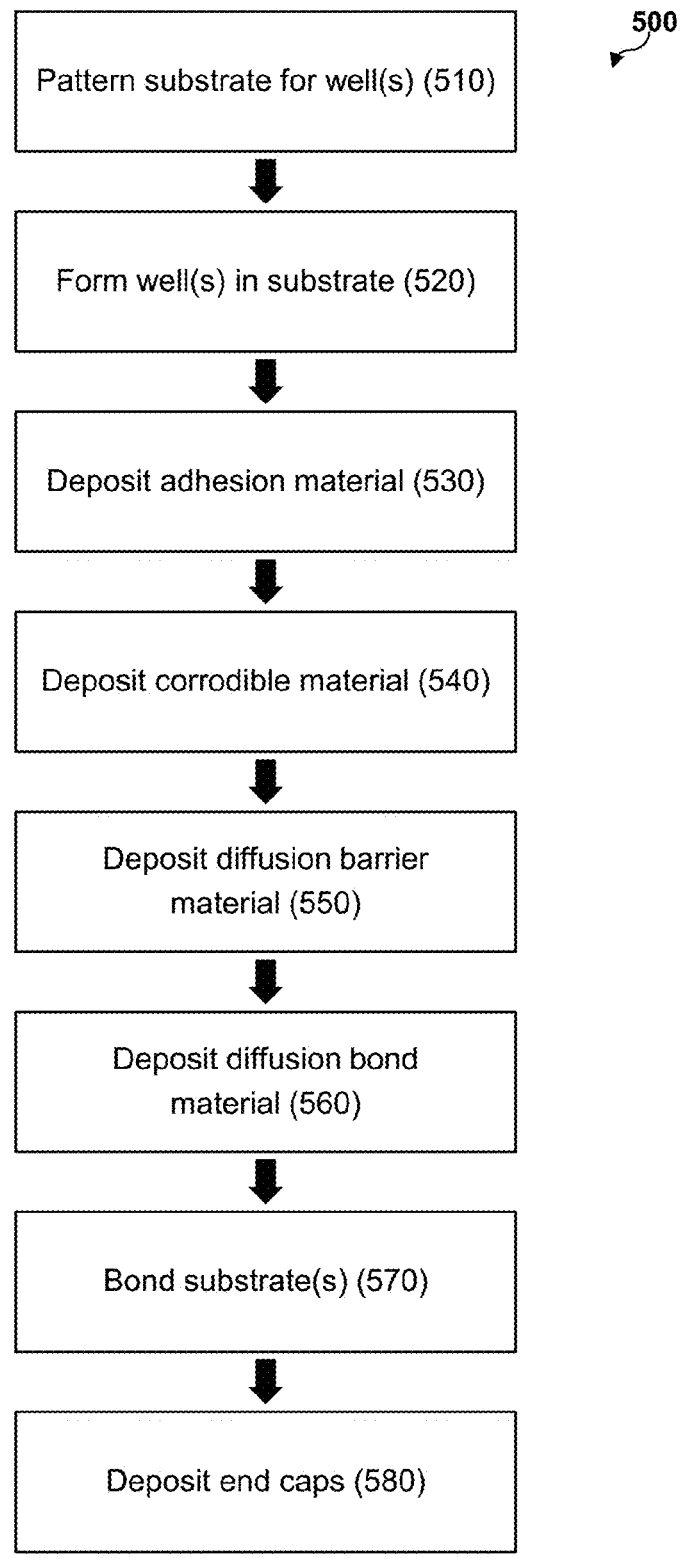
FIG. 12 shows a flow chart for an embodiment of forming a surface mount structure 500.

Also provided herein are methods for fabricating a capacitive sensor including a parallel capacitance element. FIG. 12 provides an exemplary method for fabricating a sensor having a parallel capacitance element (e.g., as shown in FIG. 11A-11C).

Referring to FIG. 12, in one embodiment, process 500 starts at a wafer level with two wafers, such as 4-inch diameter ceramic, alumina, or silicon wafers, having designated various performing multiple structures. A surface of each wafer is patterned for wells in each designated area (block 510). The wells of different substrate areas may be aligned at their width dimensions so that a well may extend laterally across the wafer resulting in wells of individual substrate areas being defined by two side walls instead of four side walls. A suitable pattern may be formed using photolithographic techniques.

Once patterned, the substrates are anisotropically etched or machined to form wells having a depth on the order of 5 microns to 400 microns. A depth of 50 microns is representative (block 520). For silicon wafers, the etch may be formed using potassium hydroxide. For alumina or other ceramic, the wells can be cut or ground by traditional machining, ultrasonics, abrasion, or other method. At least one side wall is left sloped to ensure continuous metal deposition in latter steps.

Once the wells are formed in each substrate area of each wafer, the protective photolithographic material is removed from the diffusion bond areas 605. Then, a separate photolithographic or similar protective material can be patterned along one side wall of a well in each designated substrate area for each wafer. Alternatively, the area can be protected from metal deposition by creating it as a vertical or undercut surface wall relative to the top surface of the wafer. An adhesion material (e.g., as an adhesion layer) is deposited in each substrate area (block 530).

In one embodiment, the adhesion layer is a titanium material or a chromium material (pure titanium metal, pure chromium metal) of a thickness 100 to 2000 Å, representatively 1000 Å. The adhesion layer may be deposited by CVD or sputtering technique.

Following the deposition of an adhesion material in a substrate area, a corrodible metal (e.g., as a layer) is deposited (block 540). In one embodiment, the corrodible metal is a conductive metal such as copper, aluminum, or other corrodible metal or alloy that may be deposited, e.g., by CVD or sputtering. The thickness of the corrodible metal layer may vary depending on the requirement of a structure (e.g., a requirement as a sensor or monitor). Representatively, the corrodible metal layer will have a thickness on the order of 200 Å to 10 microns, representatively, 500 Å to 2000 Å. The corrodible metal layer is deposited on the diffusion bond areas and on the substrate area.

Following the deposition of corrodible material layer, a diffusion barrier material (e.g., as a diffusion barrier layer) is deposited on the diffusion bond areas (block 550). To deposit the diffusion barrier layer on the diffusion bond areas of each structure on the wafer, the well areas are initially protected with, for example, a photolithographic mask. A suitable diffusion barrier layer material in this example is a chromium material (e.g., pure chromium) deposited to a thickness on the order of 200 Å by CVD or sputtering. Other materials are also suitable as a diffusion barrier layer material including, for example, a thin silicon nitride layer.

After the diffusion barrier layer is deposited, a diffusion bond material (e.g., as a diffusion bond layer) may also be deposited on the diffusion bond areas (block 560). A suitable diffusion bond material is gold that may be deposited to a thickness on the order of 0.1 µm to 2 µm, representatively 0.5 µm by CVD, sputtering or electroplating.

Figure 13A:
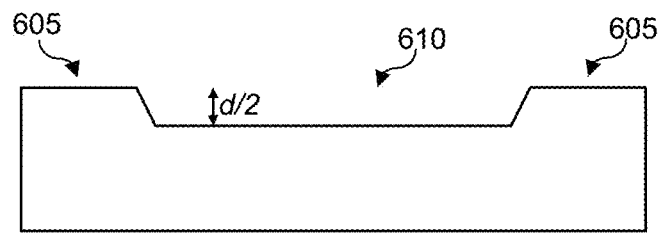
FIG. 13A-13E shows an exemplary structure area on a wafer defined by a well 610 separated by end caps. Provided are (A) a side view of the structure area prior to deposition steps, (B) a top view following deposition of an adhesion layer 620 on the end caps and in the well area exclusive of a sidewall area 615, (C) a top view following deposition of corrodible material 630 on the end caps and in the well area exclusive of a sidewall area 615, (D) a top view following deposition of an adhesion layer 640 on the end caps, and (E) a side view of the structure area after various deposition steps.
Figure 13B:
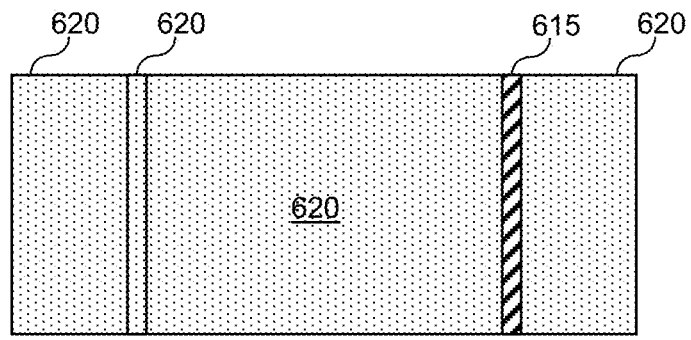
Figure 13C:
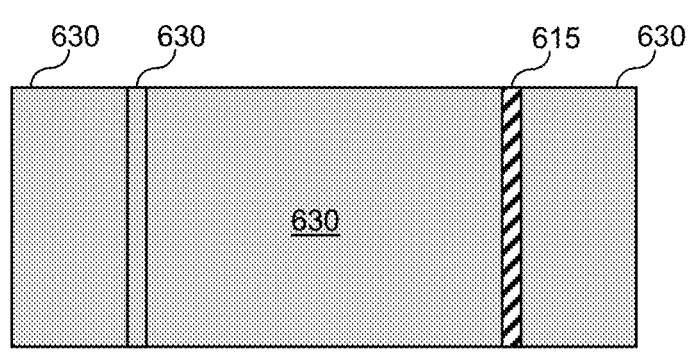

FIG. 13A-13E shows exemplary embodiments of steps 520, 530, 540, 550, and 560. FIG. 13A shows a side view of one substrate area on a wafer having been etched to form a well of depth, d/2. FIG. 13A shows a structure defined by diffusion bond areas 605 defining well 610. The protective layer to protect diffusion bond areas 605 has been removed. FIG. 13B shows a top view of one substrate area of a wafer having adhesion layer 620 deposited on the diffusion bond areas and the well area, exclusive of side wall area 615. FIG. 13C shows a top view of a substrate area of a wafer following the deposition of corrodible material 630 over the substrate area including the well and diffusion bond areas, exclusive of side wall area 615.

Figure 13D:
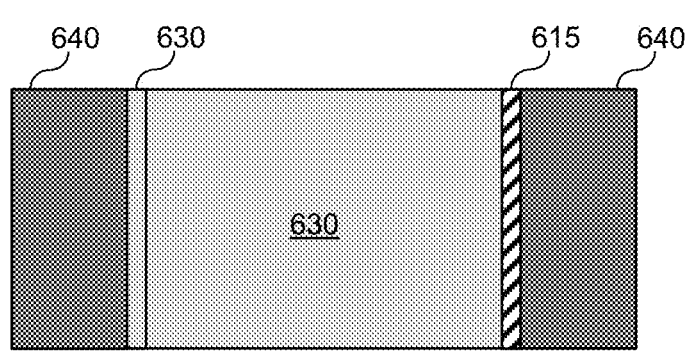

FIG. 13D shows a top view of a substrate of a wafer. In this view, the well of the substrate has as its top layer, corrodible material layer 630 as does the unprotected well side wall. Overlying each diffusion bond area (represented by identifier 640) is a composite layer of a diffusion barrier layer and a diffusion bond layer. Following the deposition of the diffusion bond area material layers, the protective mask 615 may be removed from the well and the well side wall.

Figure 13E:
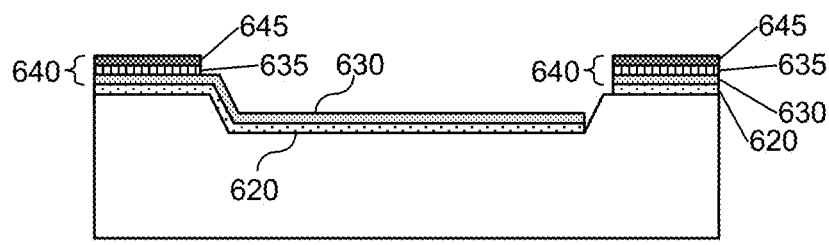

FIG. 13E shows a side view of the substrate following the removal of protective masks. FIG. 13E shows adhesion layer 620 in the well, on one well side wall, and overlying each diffusion bond area. Overlying the adhesion layer 620 is a corrodible material layer 630. Overlying the corrodible material layer 630 is a diffusion barrier layer 635. Overlying the diffusion barrier layer 635 is diffusion bond layer 645.

Figure 14:
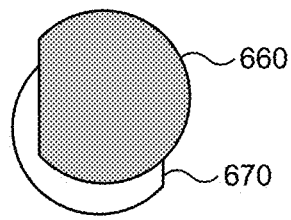
FIG. 14 shows the alignment of two wafers 660, 670 each containing a number of structure areas.

Returning to FIG. 12, where the individual substrate is formed at the wafer level, two wafers are brought together to bond opposing substrates (block 570). As shown in FIG. 14, the substrates are aligned 180 degrees rotated to one another with device layers facing each other. FIG. 14 shows wafer 660 having substrate areas patterned as described and wafer 670 also having substrate areas patterned as described being brought together so that the wells and diffusion bond areas of desired substrate areas align with one another but are transposed 180 degrees relative to one another. The wafers may be connected with one another using a low temperature diffusion bond. A photoresist mask is used to protect the corrodible material in the individual wells before bonding and possibly for protection during later processing steps.

Figure 15A:
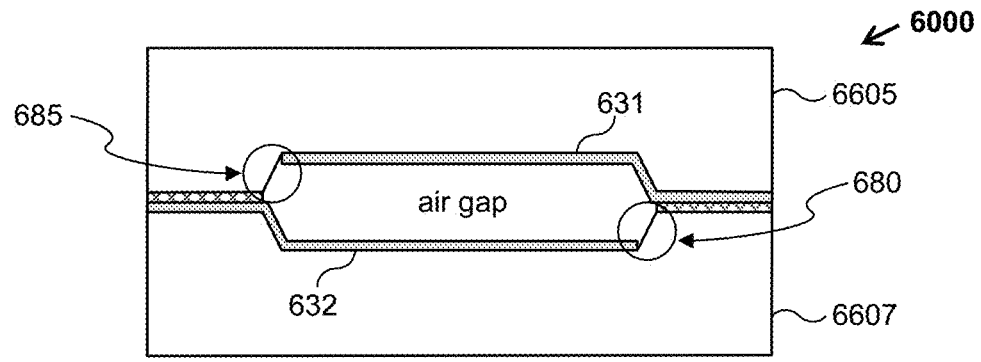
FIG. 15A-15B shows side views of a structure 6000 (A) singulated from two connected wafers 6605, 6607 and (B) patterned with end cap material layers 690 on the structure.

Following the bonding of the wafers, the composite wafer assembly is diced to create individual devices. FIG. 15A shows a singulated structure 6000 including a first substrate 6605 from a first wafer 660 and a second substrate 6607 from another wafer 670, where these substrates are bonded together with the wells of each structure area facing one another. As can be seen in FIG. 15A, the rotation of the wafers by 180 degrees relative to one another creates an area 680, 685 free of the corrodible material layer 631, 632 at opposing side walls.

Returning to FIG. 12, following the singulation of structures (bonded substrates), suitable solder pad end caps are formed (block 580). Initially, the areas of the structure other than the end cap may be protected with, for example, a photolithographic material unless already protected prior to dicing. Next, an adhesion layer of, for example, a titanium or chromium material (e.g., pure titanium, pure chromium) may be deposited to a thickness on the order of 100 to 500 Å by CVD or sputtering.

This is followed by the deposition of a solder compatible material such as nickel to a thickness of one micron to five microns by CVD or sputtering. An oxidation inhibitor layer of gold or tin may then be deposited over the solder compatible material layer by CVD, sputtering or electroplating. A suitable thickness for an oxidation inhibitor layer of gold or tin is on the order of 100 Å to 500 Å. The composite layer representing each end cap described for the solder pad end caps may cover one or more sides of the device structure, including all five sides in designated end cap areas. For electrical continuity, the composite layer is in contact with the corrodible material or a conductive material in contact with the corrodible material.

Figure 15B:
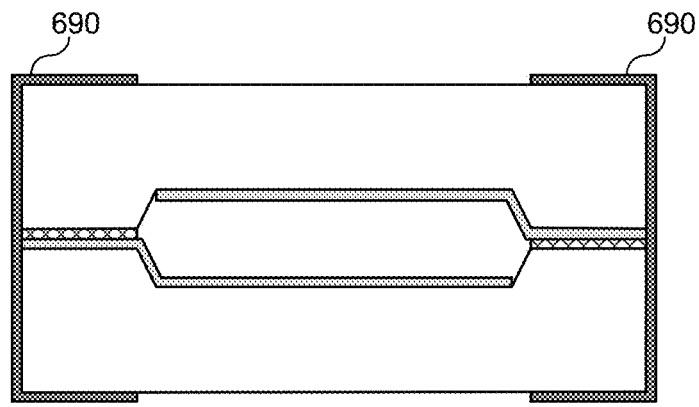

FIG. 15B shows a structure following the deposition of the composite end caps 690. FIG. 15B also shows the device structure following the removal of any photoresist or other masking material.

Integration with a PCB

The surface mount structure as used herein is a device or component that can be mounted directly on the surface of a printed circuit board. The structure described can be soldered directly onto a printed circuit board making it highly integradable with support electronics in a very small footprint. Structures may also be packaged with a high density for redundancy, extended sensing ranges, or multiple sensing tasks. Further, a sensor may be produced using standard industry methods, resulting in low per unit costs with, for example, the production of hundreds to thousands of devices per wafer.

Figure 16:
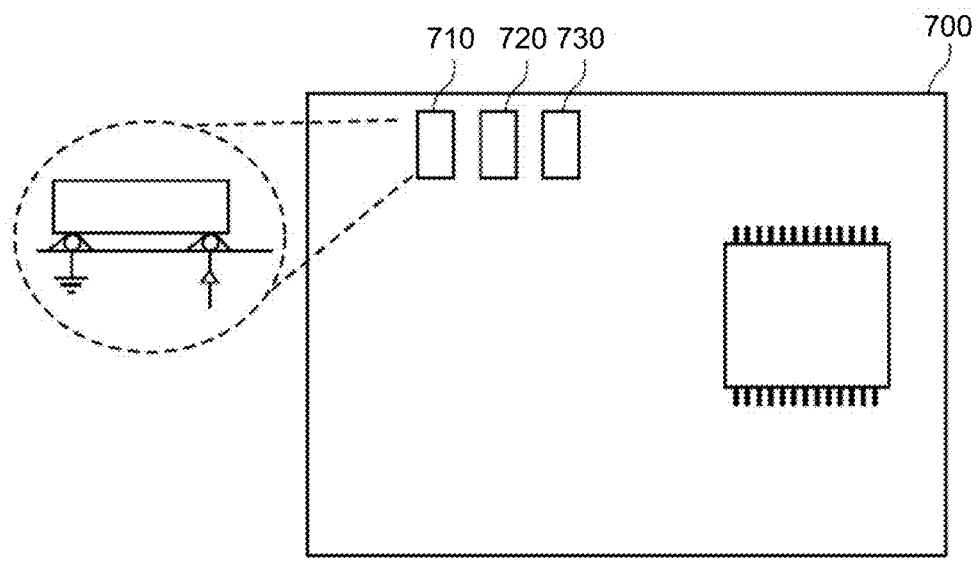
FIG. 16 shows a top view of a printed circuit board 700 having three surface mount structures connected thereto, each surface mount structure including a capacitive and/or resistive element.

FIG. 16 shows a top view of a printed circuit board. Printed circuit board 700 may include a number of devices and integrated circuits. In this embodiment, printed circuit board 700 also includes three surface mount sensor structures. FIG. 16 shows sensor structures 710, 720, and 730, and each structure has a capacitive and/or resistive element of a corrodible material. Each sensor structure is soldered to contacts on printed circuit board 700. FIG. 16 also shows a side view of sensor structure 710 and shows the structure bonded to printed circuit board 700 to solder contacts in an area corresponding to the bus bars or end caps of the structure. One bus bar or end cap of sensor structure 710 is connected to a switchable low power voltage source (e.g., DC or AC) and a second bus bar or end cap is connected to the ground.

In embodiments where multiple sensor structures are employed, such multiplicity of sensor structures may representatively be for redundancy, expanding sensing ranges or multiple sensing tasks. It is appreciated that such sensor structures need not be aligned side by side on a printed circuit board such as shown in FIG. 16, but may be individually placed as needed, such as adjacent a critical circuits. Such sensor structures may each function similarly in terms of corrosion. In this manner, each capacitive and/or resistive element may be formed of electrodes of a similar corrodible material and thickness.

Alternatively, sensing ranges can be expanded by, for example, having structures with capacitive elements of corrodible material of different thickness. For example, sensor structure 710 may have a corrodible material having a thickness of 500 Å; sensor structure 720 may have a corrodible material having a thickness of 1000 Å; and sensor structure 730 may have a corrodible material having a thickness of 1500 Å. In this manner, corrosion of sensor structure 710

(e.g., measured by a capacitance and/or resistance value) may serve as an initial warning of corrosion present at the printed structure or other platform. The subsequent corrosion of sensor structure 720 may serve as a second warning and corrosion of sensor structure 730 may serve as a final warning.

Figure 17:
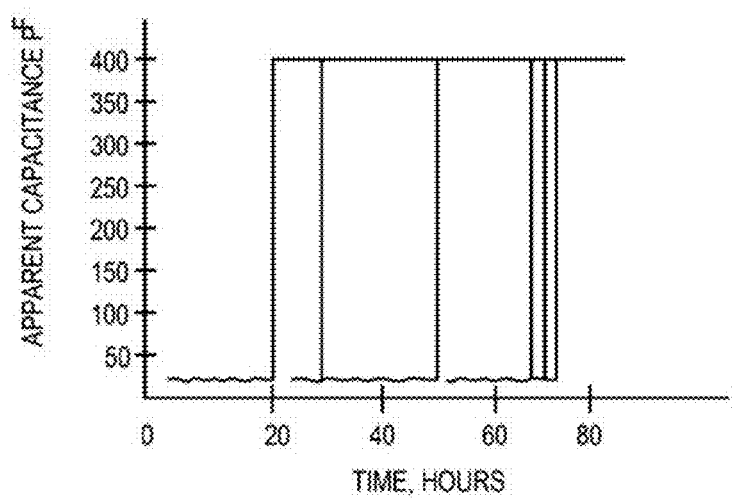
FIG. 17 shows the apparent capacitance as calculated from the resistor-capacitor (RC) time constant rise times of three surface mount structures with different corrodible thicknesses exposed to a corrosive environment over time.

The surface mount sensor including a capacitive element produced unexpected results during laboratory testing. FIG. 17 shows a plot of capacitance versus time as nine sensors of three different interdigitated electrode thicknesses (of corrodible copper) versus time as they were exposed to a corrosive environment. Capacitance values were calculated from the time it took to charge an RC circuit consisting of a fixed value mega-Ohm resistor and the corrosion capacitor. The expected result was a progressive change in capacitance during exposure to the corrosive vapors. Instead, a "switch-like" behavior was observed. Without wishing to be bound by theory, it is believed that the change in capacitance was very small, as the capacitance field lines concentrate along the edges of opposing interdigitated electrodes, passing through only a small portion of the corroding material followed by a large air gap.

A much larger change is observed when the copper corrodes down to the adhesion layer, which, in this example, is a 200 Å thick titanium film. The titanium film becomes even thinner upon application to the substrate (e.g., an alumina substrate) as it oxidizes to form a strong covalent bond with the substrate. The resistance of this thin titanium layer is on par with the fixed resistor, creating a significant shift in the RC time constant. The titanium layer is electrically in series with the fixed resistor. The RC time constant then becomes $(R1+R2)*C$, where R1 is the fixed resistor and R2 is the resistance of the capacitive sensor. The switch-like behavior occurs when R2 becomes significant (titanium is a resistive metal), greatly slowing the charging time of the capacitive sensor.

Figure 18:
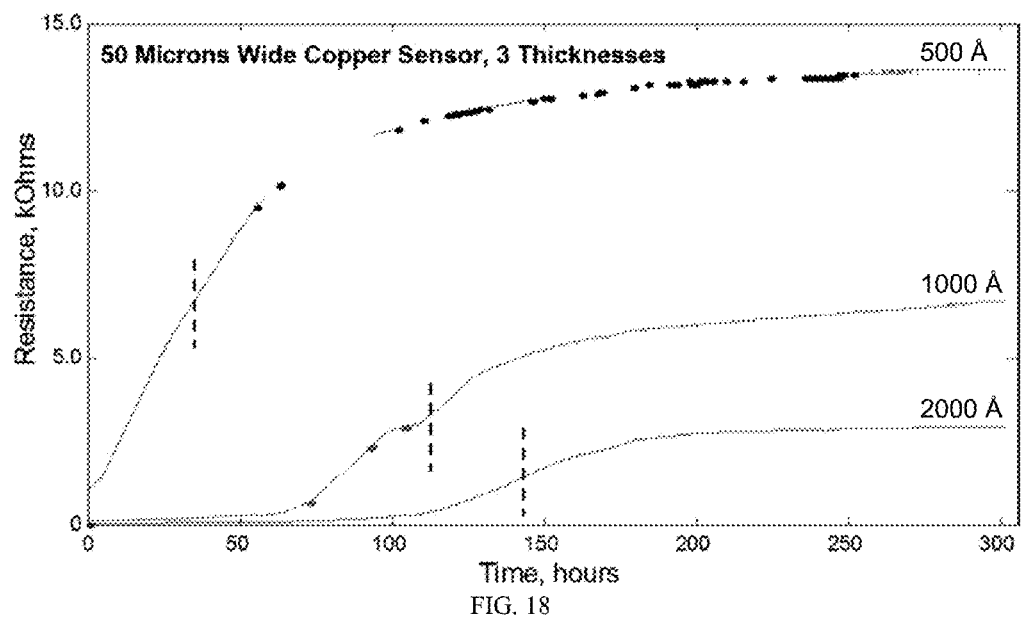
FIG. 18 shows a graph of resistance as a function of time for three 50 micron wide resistive sensors tested in a highly corrosive environment (moist hydrogen sulfide). Dashed vertical lines indicate ΔR/R equals 50%.

FIG. 18 shows switching behavior for three resistive sensors, where each has a different thickness (i.e., 500 Å, 1000 Å, or 2000 Å of copper). The switching behavior illustrated in FIGS. 17 and 18 can be taken advantage of in corrosion sensing. Thicker layers of a corrodible material such as copper take progressively longer to corrode down to the adhesion layer. The time till switching occurs for a given thickness provides information on the corrosive potential of the surroundings. A series of progressively thicker copper coatings will switch in order according to their thicknesses. If sensor coating thickness approaches fractions of a micron, deeper corrosion becomes slower as copper and, for example, sulfur migrate through the existing corrosive crusts, and the rate of corrosion slows, extending the life of the thicker sensors.

Although FIG. 17 demonstrated the behavior of interdigitated electrode structures (such as any described herein), a similar behavior is anticipated with the structures described with reference to FIGS. 11A-11C, 13A-13E, 14, and 15A-15B. If the switch-like behavior is not desired, a different arrangement of electrodes is possible. Opposing plate electrode structures can be microfabricated in the same printed circuit board mountable design. For these structures, the capacitive field lines pass directly through the corroding surface plates and the air gap in-between. Making the plates much larger, renders the edge effects a small portion of the sensing area (e.g., a much thicker and conductive metal layer between the adhesion metal (titanium or chromium) with thick nickel and thick copper). The corroding copper modifies the capacitance of the capacitive sensor. By using a thick, electrically conducting, underlying non-corrosive metal layer little or no effective change in the internal resistance of the structure will occur to confound the RC time constant measurement. The predominant cause of change will then be due to the change in capacitance alone. A thin electrically conducting, underlying, non-corrosive metal layer may be used to include the switch-like behavior at the end of the structure's useful life.

Uses

The structure described herein for use as a sensor can be incorporated into building ventilation systems, behind wall board, in first responder respirators, household or high consequence electronics (e.g., aviation, weapon system, etc.), water monitoring systems, space systems, automotive systems, architectural structures, environmental change indicates, remote-based systems, and potentially corrosive environments (e.g., such as in deep well, gas, oil, or geothermal locations), as well as various other locations.

EXAMPLES

Example 1

PC Board Mount Corrosion Monitors

We have created sensors designed and microfabricated in the style of standard surface mount components (such as resistors and capacitors) found on printed circuit boards (PCB). These can be soldered directly onto PCBs, making them highly integrable with support electronics in a very small footprint. They can also be packaged with a high density for redundancy, expanded sensing ranges, or multiple sensing tasks. Many of the sensors are produced using standard industry methods, resulting in low per unit costs with hundreds of devices per wafer (e.g., 600 sensors from a single 4" wafer). To date sensors have been designed for corrosion or copper, aluminum and wire bonded chips. Many other systems are possible.

Figure 19A:
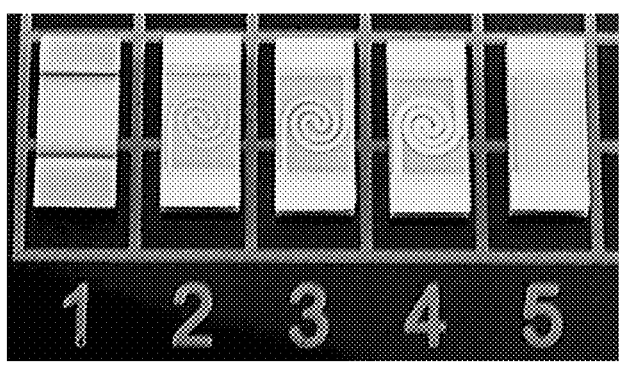
FIG. 19A-19B shows photographs of (A) PC mount corrosion resistive sensors of various serpentine widths (labeled 2, 3, and 4), a PC mount capacitive sensor (labeled 5), and a reference sensor (labeled 1); and (B) an exemplary serpentine corrosion resistive sensor.
Figure 19B:
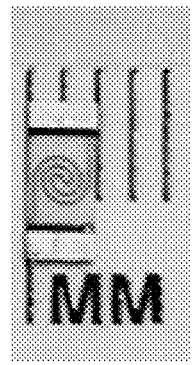
Figure 20A:
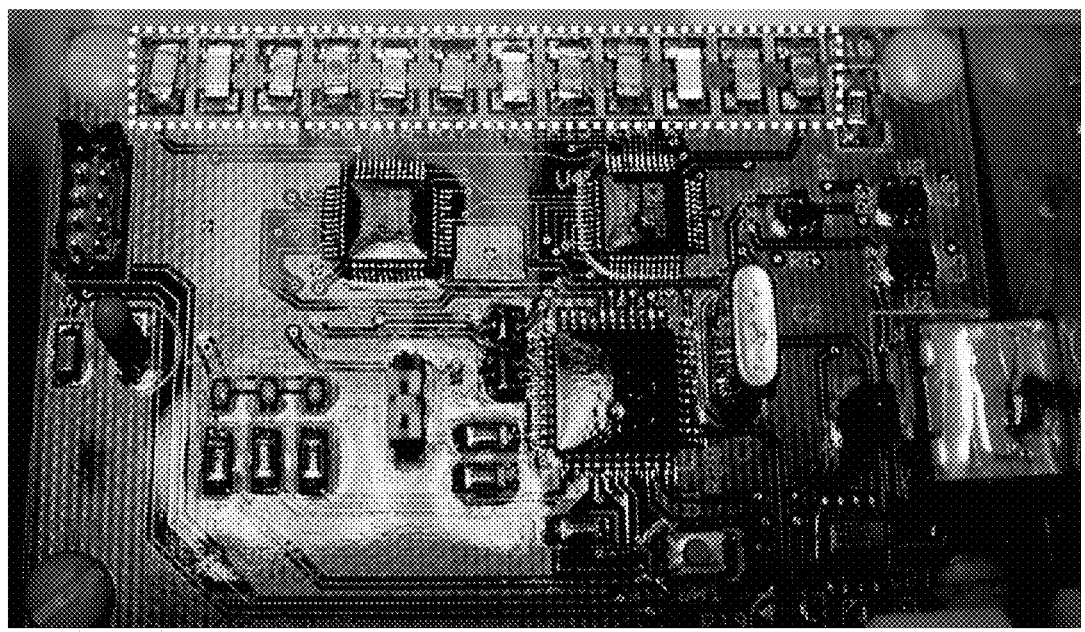
FIG. 20A-20B shows photographs of (A) a line of corrosion sensors of various widths and thickness (indicated by white dashed lines) soldered to a PC board and (B) an exemplary PC board mounted corrosion resistive sensor.
Figure 20B:
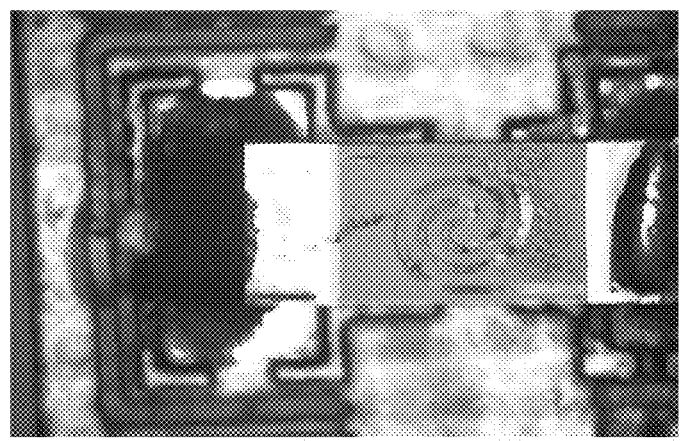

The sensors described here are fabricated in large quantities using microfabrication techniques. FIG. 18 is a graph showing resistance as a function of time. The dashed vertical lines indicate $\Delta R/R$ equals 50%, which can be optionally used as the switching point for corrosion sensing. In non-limiting examples, practical sensor dimensions range from 0.010"× 0.010" to 0.5"×0.5". FIG. 19A-19B provides photographs of exemplary sensors. It is the small size and solder pad configuration that allows these sensors to be easily integrated with electronic circuitry directly on printed circuit boards (PCBs). FIG. 20A-20B provides photographs of PCB mounted sensors.

Automated "pick and place" systems can populate and solder entire circuit boards in large production quantities. The size of the sensor also allows incorporation of many sensors in a small area to increase the functionality of the sensing system in terms of range, type, or for surety through redundancy. Sensors can be incorporated into building ventilation systems, behind wallboard, in first responder respirators, household or high consequence electronics, water monitoring systems, architectural structures (buildings, bridges, etc.), automotive systems, space systems, environmental change indicators, remote-based systems, and a great many other locations. Another possible benefit is minimal power consumption, as the sensor accumulates corrosion effects passively, and power is needed only when interrogating.

The sensor can be formed from any useful material. For instance, the sensor substrate can be ceramic, silicon, or any other useful substrate material compatible with microfabrication processes. The substrate can be one onto which solder or bond pads are photolithographically defined. Active structures, such as corrodible copper, may be photolithographically defined at this time as well, or added in subsequent steps.

The individual sensors can then be diced into sizes typical of surface mount resistors and capacitors found on circuit boards. The solder pads including the sides are then coated with a thin layer (200 Å) of titanium or other adhesion metal, and a thick layer of nickel for soldering. A thin protective layer of gold protects the nickel from oxidation, which otherwise can hamper soldering. The pads can also be tinned to facilitate soldering to printed circuit boards. A strip of nickel without a protective layer can be created near any sensitive structures to serve as a solder dam once exposure to air oxidizes it.

Example 2

Capacitive Corrosion Sensors

The corrosion sensors of the invention can be configured to facilitate integration or coupling to a PCB. For instance, most capacitor and resistor components are provided in various sizes, as determined under industry standards. For instance, size code 1808 (metric code 4520) provides a component having a length L of about 0.18" and a width W of about 0.080" or 4.57 mm×2.03 mm (L×W) in metric units. Other size codes include code 0805 (metric 2012) for a 0.079"× 0.049" (2.0 mm×1.25 mm) component; 1210 (metric 3225) for a 0.126"×0.098" (3.2 mm×2.5 mm) component; and code 2010 (metric 5025) for a 0.197"×0.098" (5.0 mm×2.5 mm) component, all provided as L×W. Other size codes are known. Thus, the corrosion sensors of the invention can be configured to have any useful footprint and dimensions consistent with known size codes.

Figure 21A:
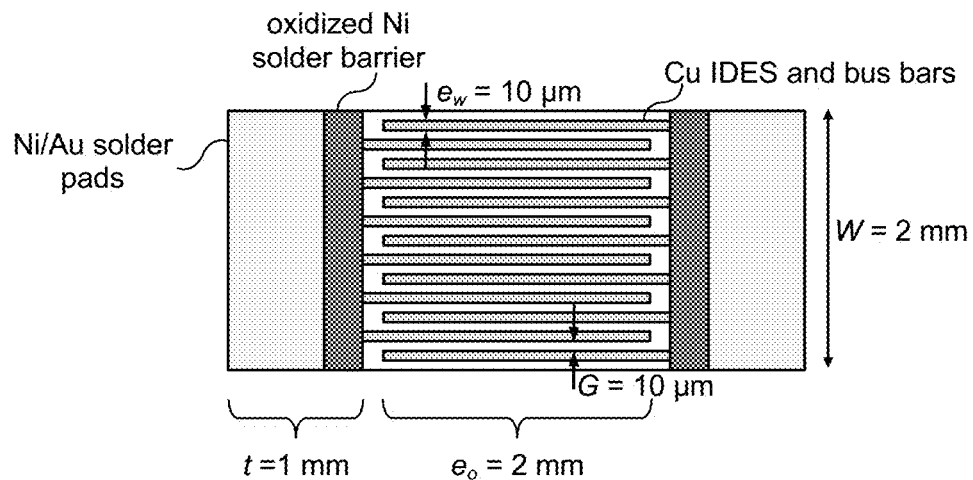
FIG. 21A-21C shows a schematic of an exemplary capacitive sensor. Provided are (A) top, (B) side, and (C) end views of a sensor having 50 interdigitated electrode pairs, where only a few are shown for clarity. The thickness of the electrode $e_t$ can be optimized to provide various sensing ranges.
Figure 21B:
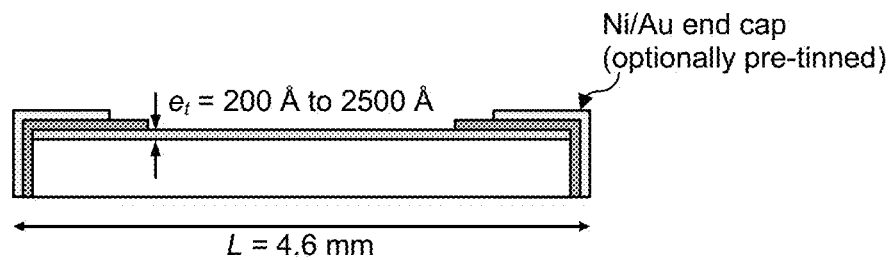
Figure 21C:
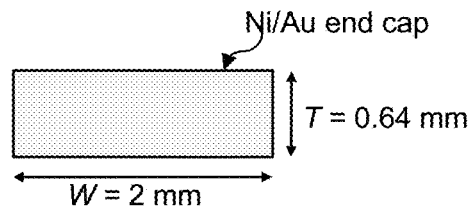

FIG. 21A-21C provides an exemplary capacitive corrosion sensor having size 1808. This standardized size, while not required, can aid PCB design. For instance, the sensor can have the following dimensions: L is about 4.57±0.25 mm (0.180±0.015"); W is about 2.03±0.25 mm (0.080±0.015"); T is about 0.64±0.10 mm (0.025", e.g., 0.065" maximum); and t is about 1.0 mm (0.040±0.02") or about 0.51 mm±0.25 (0.020±0.010") (see FIG. 6 providing dimension parameters). In one example, the sensor has the following dimensions: L is about 4.6 mm; W is about 2 mm; T is about 0.64 mm; and t is about 1 mm.

The exemplary sensor includes 50 pairs of interdigitated electrode (IDE) pairs having an electrode width $e_w$ of 10 μm and a gap G of 10 μm (FIG. 21A). The IDEs and bus bars are formed of copper. Bare oxidized nickel layers provide a solder barrier, which keeps solder away from sensitive structures. In addition, gold-plated nickel solder pads are provided, which are disposed over the copper bus bar and wrapped down over the ends.

The electrode can have any useful thickness $e_t$ (FIG. 21B). For instance, the thickness can be optimized to provide various sensing ranges, and non-limiting $e_t$ includes of from about 200 Å to 2500 Å.

The sensor also includes end caps located on the ends of the sensor (FIG. 21B-21C). The end caps provide an electrical connection to the PCB and, optionally, can include one or more coatings to facilitate soldering of the sensor to the PCB. For instance, the end cap can be an Ni/Au composite layer with a pre-tinned layer.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated in the figure to indicate corresponding or analogous elements, which may optionally have similar characteristics.

It should also be appreciated that reference throughout this specification to "one embodiment," "an embodiment," "one or more embodiments," or "different embodiments," for example, means that a particular feature may be included in the practice of the invention. Similarly, it should be appreciated that in the description, various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

The invention claimed is:

1. An apparatus comprising one or more surface mount structures, wherein at least one surface mount structure comprises: a capacitive element having a property that is responsive to an environmental condition, and
    wherein the at least one surface mount structure comprises dimensions suitable for mounting on a printed circuit board.

2. The apparatus of claim 1, wherein the capacitive element comprises a corrodible metal and the at least one or more surface mount structures further comprises a resistive element, and wherein a time constant associated with the at least one or more surface structures change once the corrodible metal corrodes to reflect a resistance of the resistive element.

3. The apparatus of claim 2, wherein the capacitive and/or the resistive element comprises a corrodible metal coupled to an adhesion layer on a substrate and wherein the adhesion layer comprises a conductive metal.

4. The apparatus of claim 3, wherein the corrodible metal comprises copper.

5. The apparatus of claim 4, wherein the conductive metal of the adhesion layer comprises titanium.

6. The apparatus of claim 1, wherein the capacitive element comprises a corrodible metal configured as a pair of interdigitated electrodes.

7. The apparatus of claim 1, wherein the capacitive element comprises opposing electrodes separated by an air gap.

8. The apparatus of claim 2, wherein the resistive element comprises a corrodible metal having a serpentine configuration.

9. An apparatus comprising a plurality of surface mount structures, wherein at least one surface mount structure is coupled to a printed circuit board at a first contact point associated with a power circuit and at a second point associated with a ground, and wherein the at least one surface mount structure comprises a capacitive and a resistive element having a property that is responsive to an environmental condition.

10. The apparatus of claim 9, wherein the capacitive and the resistive element comprises a corrodible metal.

11. The apparatus of claim 10, wherein the corrodible metal comprises copper.

12. The apparatus of claim 9,
wherein the apparatus further comprises a second surface mount structure comprising a second capacitive and a second resistive element coupled to the printed circuit board,
wherein each of the capacitive, the resistive element, the second capacitive and the second resistive element comprises a corrodible metal defined by a layer thickness, and
wherein the layer thickness of the corrodible metal of the first surface mount structure is different than the layer thickness of the corrodible metal of the second surface mount structure.

13. The apparatus of claim 9, wherein the capacitive and the resistive element comprises a corrodible metal, wherein the corrodible metal is coupled to an adhesion layer.

14. The apparatus of claim 13, wherein the adhesion layer comprises a conductive metal.

15. The apparatus of claim 9, wherein the capacitive element of the surface mount structure comprises a corrodible metal configured as a pair of interdigitated electrodes.

16. The apparatus of claim 9, wherein the capacitive element comprises opposing electrodes separated by an air gap.

17. The apparatus of claim 9, wherein the resistive element comprises a corrodible metal having a serpentine configuration.

18. The apparatus of claim 9, wherein each surface mount structure is coupled to the printed circuit board.

19. A method comprising:
providing at least one surface mount sensor proximate to an electrical component, the at least one surface mount sensor comprising a capacitive and a resistive element having a property that is responsive to an environmental condition;
measuring a capacitance value and/or a resistance value of the at least one surface mount sensor; and
relating a measured capacitance and/or resistance to a corrosion experienced by the electrical component.

20. The method of claim 19, wherein the measuring the capacitance value comprises determining a time to charge an RC circuit comprising a resistor.

21. The method of claim 19, further comprising providing a plurality of surface mount sensors proximate to the electrical component, wherein each of the plurality of surface mount sensors comprises a corresponding capacitive and/or a corresponding resistive element, wherein the corresponding capacitive and/or the corresponding resistive element comprises a corrosive metal, and wherein a thickness of the corrosive metal is progressively greater starting from a first terminus of a first surface mount sensor of the plurality of surface mount sensors to a second terminus of a last surface mount sensor of the plurality of surface mount sensors.

22. The apparatus of claim 1, wherein each surface mount structure is coupled to the printed circuit board.

* * * * *